US008273366B2

(12) United States Patent
Chauhan et al.

(10) Patent No.: US 8,273,366 B2
(45) Date of Patent: *Sep. 25, 2012

(54) OPHTHALMIC DRUG DELIVERY SYSTEM

(75) Inventors: Anuj Chauhan, Gainesville, FL (US); Derya Gulsen, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1135 days.

This patent is subject to a terminal disclaimer.

(21) Appl. No.: 10/802,058

(22) Filed: Mar. 17, 2004

(65) Prior Publication Data

US 2004/0241207 A1 Dec. 2, 2004

Related U.S. Application Data

(63) Continuation-in-part of application No. 10/454,836, filed on Jun. 5, 2003.

(60) Provisional application No. 60/385,571, filed on Jun. 5, 2002.

(51) Int. Cl.
*A61K 9/00* (2006.01)
(52) U.S. Cl. ..................................................... 424/429
(58) Field of Classification Search .................. None
See application file for complete search history.

(56) References Cited

U.S. PATENT DOCUMENTS

| 3,786,812 | A | * | 1/1974 | Neefe | 424/429 |
| 3,937,680 | A | | 2/1976 | de Carle | 260/29.6 |
| 3,957,049 | A | | 5/1976 | Neefe | |
| 4,052,505 | A | * | 10/1977 | Higuchi et al. | 424/427 |
| 4,254,509 | A | | 3/1981 | Tennant | 3/13 |
| 4,484,922 | A | | 11/1984 | Rosenwald | 424/427 |
| 4,668,506 | A | | 5/1987 | Bawa | 424/429 |
| 4,925,017 | A | * | 5/1990 | Jessen | 206/5.1 |
| 4,959,217 | A | | 9/1990 | Sanders et al. | 424/473 |
| 5,723,131 | A | | 3/1998 | Schultz et al. | 424/400 |
| 5,891,932 | A | * | 4/1999 | Benz et al. | 523/106 |
| 6,027,745 | A | | 2/2000 | Nakada et al. | |
| 6,201,065 | B1 | | 3/2001 | Pathak et al. | 525/90 |
| 6,221,399 | B1 | | 4/2001 | Rolfes | |
| 6,264,971 | B1 | * | 7/2001 | Darougar et al. | 424/427 |
| 6,284,161 | B1 | | 9/2001 | Thakrar et al. | |
| 6,410,045 | B1 | | 6/2002 | Schultz et al. | 424/429 |
| 2002/0141760 | A1 | * | 10/2002 | Resnick | 396/661 |
| 2003/0216431 | A1 | * | 11/2003 | Raut | 514/313 |

FOREIGN PATENT DOCUMENTS

EP 0480690 * 10/1991

OTHER PUBLICATIONS

Nagarsenker et al, Preparation and Evaluation of Liposomal Formulations of Tropicamide for Ocular Delivery, Int. Journal of Pharmaceutics 190 (1999) 63-71.*
Paul et al , Uses and Applications of Microemulsions, Current Science, vol. 80, No. 8, Apr. 25, 2001, 990-1001.*
Ding, Reent Developments in Ophthalmic Drug Delivery, PSTT vol. 1, No. 8 Nov. 1998, 328-335.*
Vandamme, Microemulsions as Ocular Drug Delivery Systems: Recent Developments and Future Challenges, Progress in Retinal and Eye Research 21 (2002) 15-34.*
Ghosh, Hydrophilic Polymeric Nanoparticles as Drug Carriers, Indian Journal of Biochemistry & Biophysics, vol. 37, Oct. 2000, pp. 273-282.*
Seijo et al, Design of nanoparticle of less than 50nm diameter: preparation, characterization and drug loading, Int. Journal of Pharmaceutics, vol. 62, Issue 1, Jul. 15, 1990, Abs.*
Nagarsenker, M.S., Londhe, V.Y., Nadkarni, G.D., "*Preparation and evaluation of liposomal formulations of tropicamide for ocular delivery*", Int. J. of Pharm., 1990, 190: 63-71.
Bourlais, C.L., Acar, L., Zia H., Sado, P.A., Needham, T., Leverge, R., "*Ophthalmic drug delivery systems*", Progress in retinal and eye research, 1998, 17, 1:33-58.
Lang, J.C., "*Ocular drug delivery conventional ocular formulations*". Adv. Drug Delivery, 1995, 16: 39-43.
Segal, M., "*Patches, pumps and timed release*", FDA Consumer magazine, Oct. 1991.
Hehl, E.M., Beck, R., Luthard K., Guthoff R., "*Improved penetration of aminoglycosides and fluoroquinolones into the aqueous humour of patients by means of Acuvue contact lenses*", European Journal of Clinical Pharmacology, 1999, 55 (4): 317-323].
Hillman,J.S., "Management of acute glaucoma with Pilocarpine-soaked hydrophilic lens" Brit.J.Ophthal.58 (1974) p. 674-679.
Ramer,R. and Gasset,A., "Ocular Penetration of Pilocarpine:" Ann. Ophthalmol.6, (1974) p. 1325-1327.
Montague Ruben. and Watkins,R., "Pilocarpine dispensation for the soft hydrophilic contact lens" Brit.J.Ophthal. 59, (1975) p. 455-458.
Hillman,J.,Marsters,J. and Broad,A."Pilocarpine delivery by hydrophilic lens in the management of acute glaucoma" Trans. Ophthal.Soc.U.K. (1975) p. 79-84.
Giambattista,B.,Virno,M., Pecori-Giraldi,Pellegrino,N. and Motolese,E. "Possibility of Isoproterenol Therapy with Soft Contact Lenses: Ocular Hypotension Without Systemic Effects" Ann. Ophthalmol 8 (1976) p. 819-829.
Marmion,V.J. and Yardakul,S. "Pilocarpine administration by contact lens" Trans.Ophthal.Soc.U.K.97, (1977) p. 162-3.
Elisseeff, J., McIntosh, W., Anseth, K., Riley, S., Ragan, P., Langer, R., "*Photoencapsulation of chondrocytes in poly(ethylene oxide)-based semi-interpenetrating networks*", Journal of Biomedical Materials Research, 2000, 51 (2): 164-171.
Ward, J.H., Peppas, N.A., "*Preparation of controlled release systems by free-radical UV polymerizations in the presence of a drug*", Journal of Controlled Release, 2001, 71 (2): 183-192.

(Continued)

Primary Examiner — Tracy Vivlemore
Assistant Examiner — Jennifer Berrios
(74) Attorney, Agent, or Firm — Miles & Stockbridge P.C.; David R. Schaffer, Esq.

(57) ABSTRACT

A drug delivery system comprising a contact lens having dispersed therein as nanoparticles having a particle size less than about 200 nm, an ophthalmic drug nanoencapsulated in a material from which said ophthalmic drug is capable of diffusion into and migration through said contact lens and into the post-lens tear film when said contact lens is placed on the eye.

21 Claims, 19 Drawing Sheets

OTHER PUBLICATIONS

Scott, R.A., Peppas, N.A., "*Highly crosslinked, PEG-containing copolymers for sustained solute delivery*", Biomaterials, 1999, 20 (15): 1371-1380.

Podual, K., Doyle F.J., Peppas N.A., "*Preparation and dynamic response of cationic copolymer hydrogels containing glucose oxidase*", Polymer, 2000, 41 (11): 3975-3983.

Colombo, P., Bettini, R., Peppas, N.A., "*Observation of swelling process and diffusion front position during swelling in hydroxypropyl methyl cellulose (HPMC) matrices containing a soluble drug*", Journal of Controlled Release, 1999, 61 (1,2): 83-91.

Ende, M.T.A., Peppas, N.A., "*Transport of ionizable drugs and proteins in crosslinked poly(acrylic acid) and poly(acrylic acid-co-2-hydroxyethyl methacrylate) hydrogels. 2. Diffusion and release studies*", Journal of Controlled Release, 1997, 48 (1): 47-56.

Graziacascone, M., Zhu, Z., Borselli, F., Lazzeri, L., "*Poly(vinyl alcohol) hydrogels as hydrophilic matrices for the release of lipophilic drugs loaded in PLGA nanoparticles*", Journal of Material Science: Materials in Medicine, 2002, 13: 29-32.

Mandell, R.B., "*Contact Lens Practice: Hard and Flexible Lenses*", $2^{nd}$ ed., Charles C. Thomas, Springfield, vol. 3, 1974.

Creech, J.L., Chauhan, A., Radke, C.J., "*Dispersive mixing in the posterior tear film under a soft contact lens*", I&EC Research, 2001, 40: 3015-3026.

McNamara, N.A., Polse, K.A., Brand, R.D., Graham, A.D., Chan, J.S., McKenney, C.D., "*Tear mixing under a soft contact lens: Effects of lens diameter*". Am. J. of Ophth., 1999, 127(6): 659-65.

Arriagada, F.J., Osseo-Asare, K., "*Synthesis of nanosize silica in a nonionic water-in-oil microemulsion: effects of the water/surfactant molar ratio and ammonia concentration*", Journal of Colloid & Interface Science 1999, 211: 210-220].

Letter from Korean Associate dated May 10, 2008, informing of Office Action issued on Apr. 27, 2008 for corresponding Korean Patent Application No. 2004-7019648 based on International application No. PCT/US03/17736 for "Ophthalmic Drug Delivery System".

\* cited by examiner

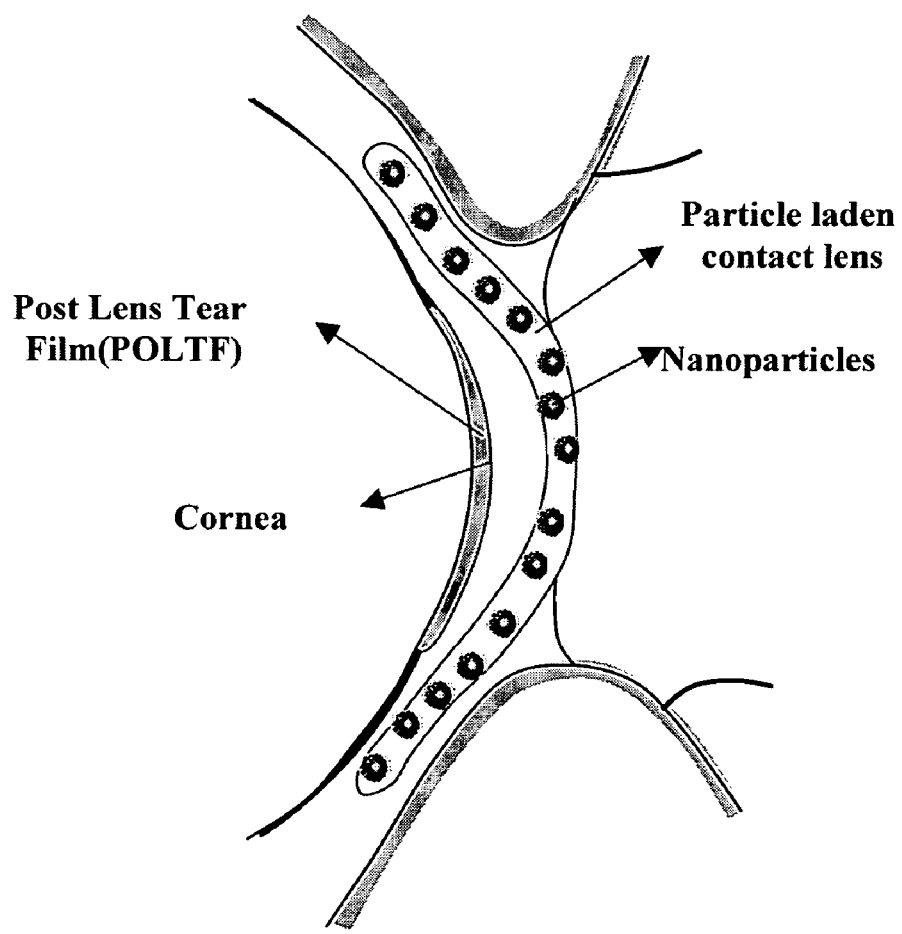
Figure 1: Schematic of the particle laden lens inserted in the eye

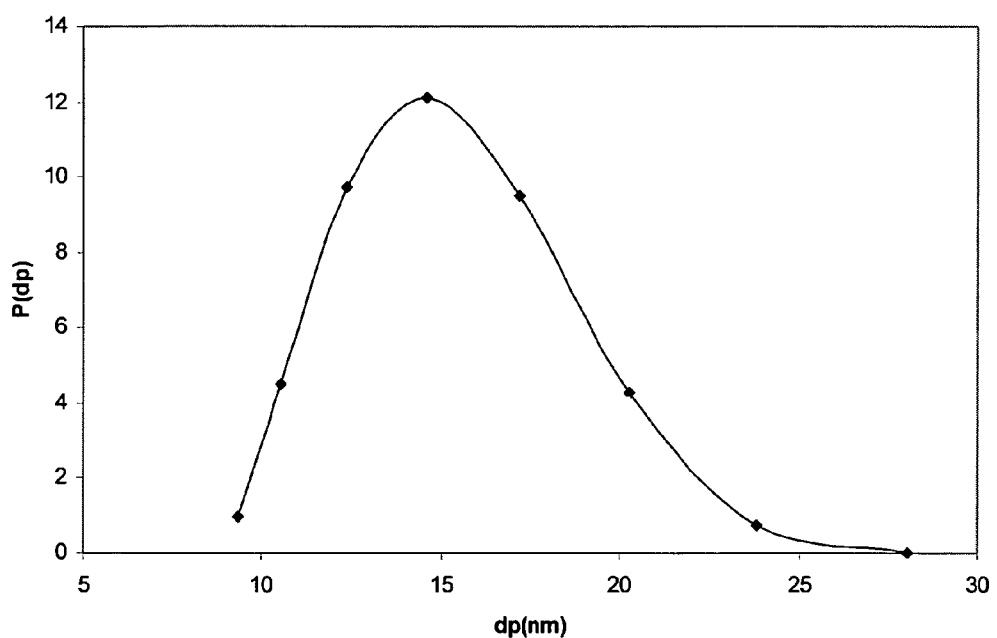
Figure 2: Particle size distribution for Type 1 (Canola oil/Water microemulsion stabilized by Tween 80 and Panadon SDK) microemulsion

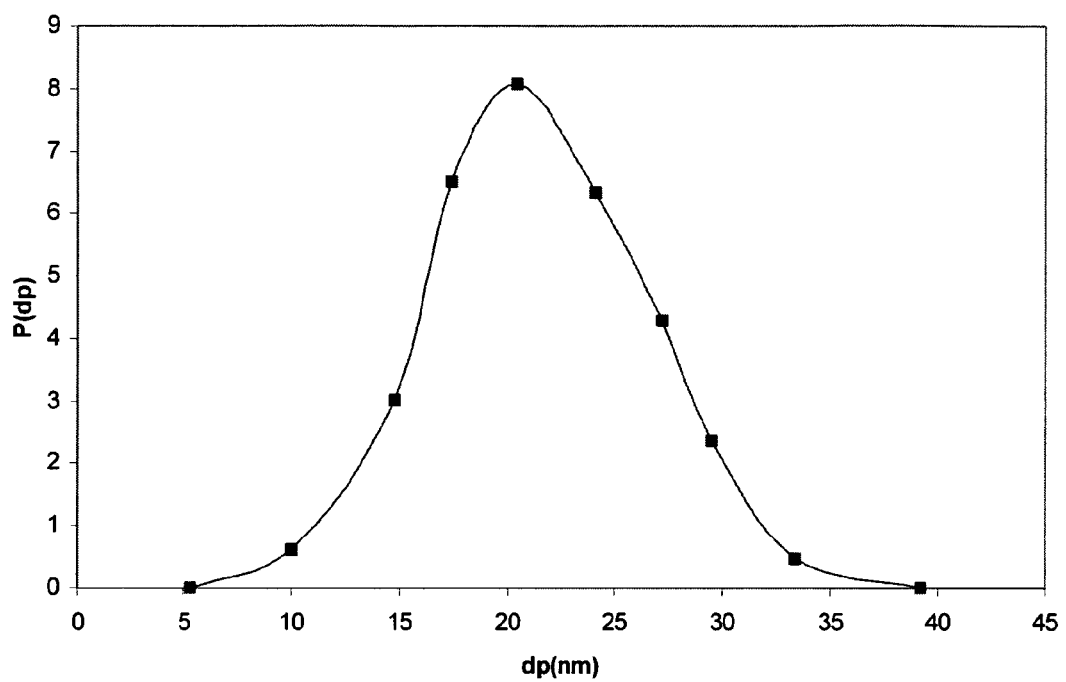
Figure 3: Figure 2: Particle size distribution for Type 2 (Canola oil/Water microemulsion stabilized by Tween 80 and Panadon SDK and a silica shell) microemulsion

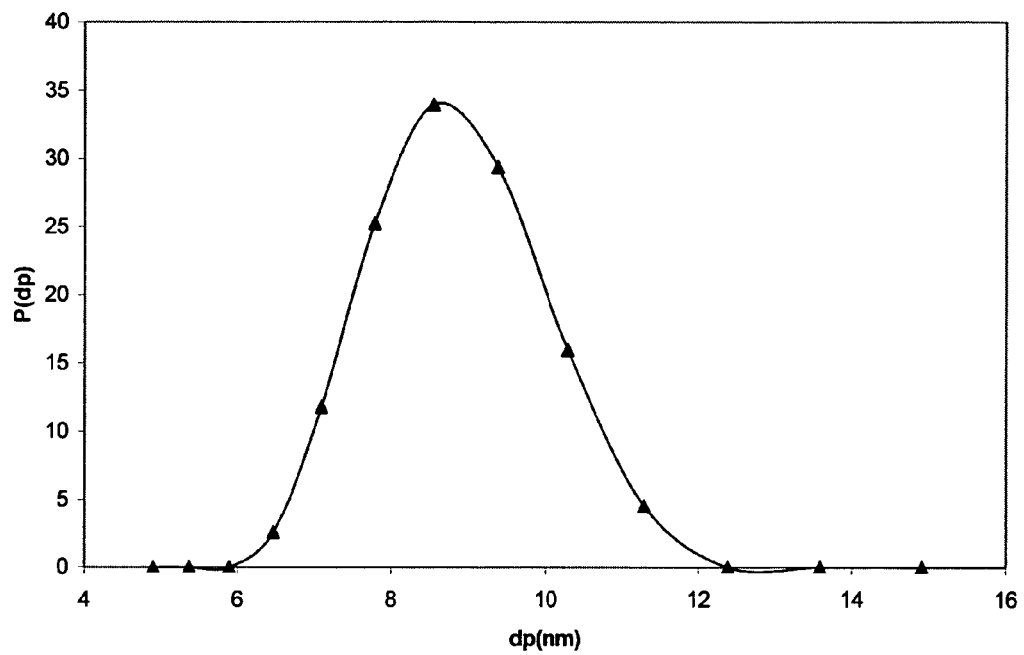
Figure 4: Particle size distribution for Type 3 (Hexadecane/ Water microemulsion stabilized by Brij 97) microemulsion

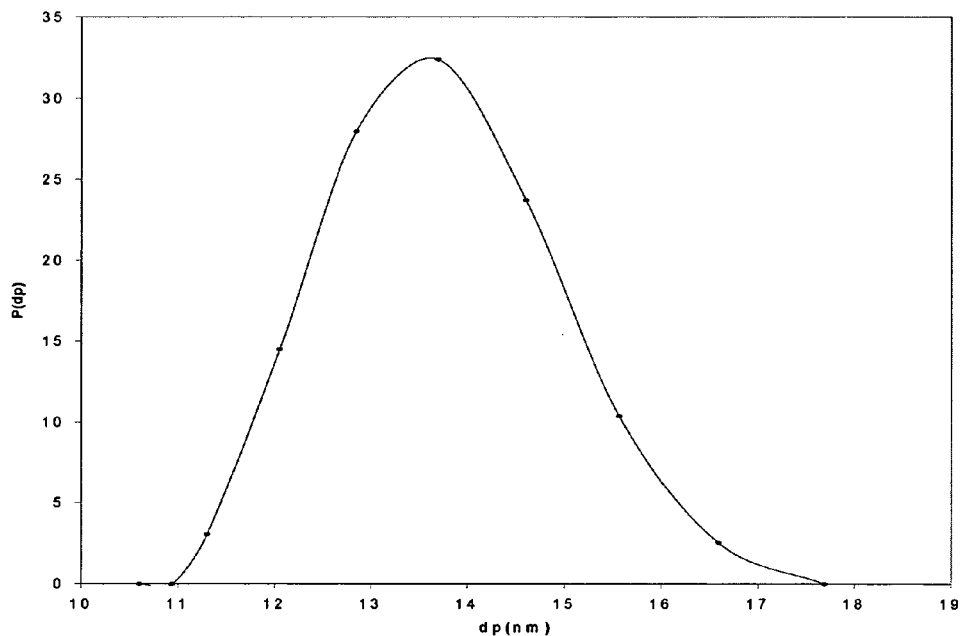
Figure 5: Particle size distribution for Type 4 (Hexadecane/ Water microemulsion stabilized by Brij 97 and a silica shell) microemulsion

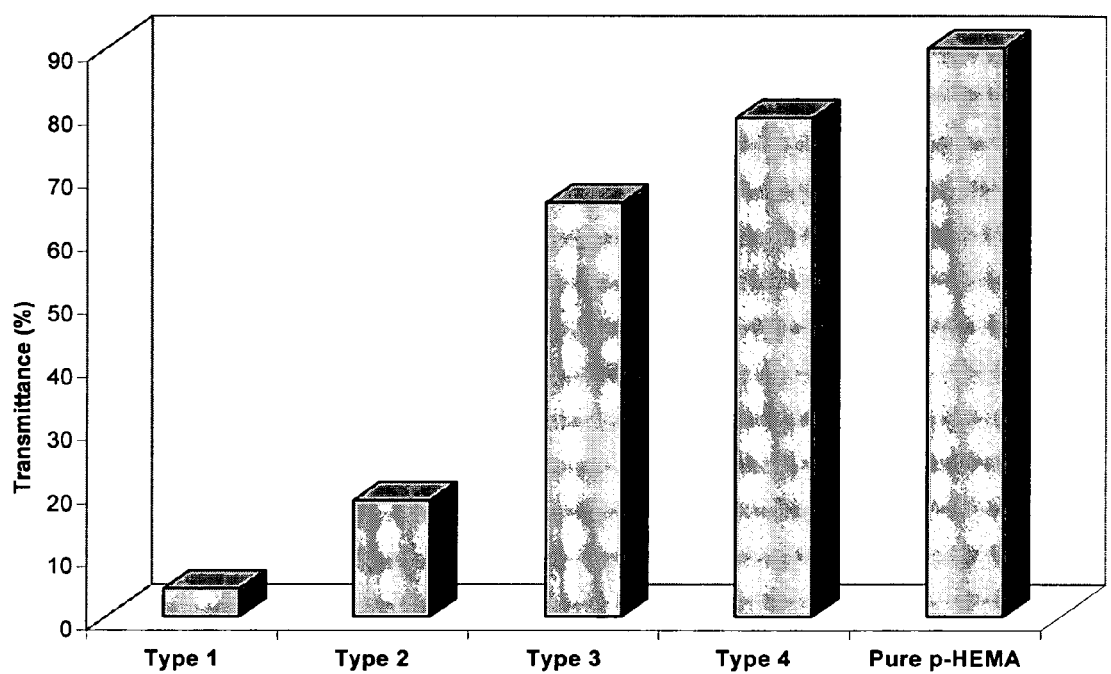
Figure 6: Transmittance values of different hydrogels

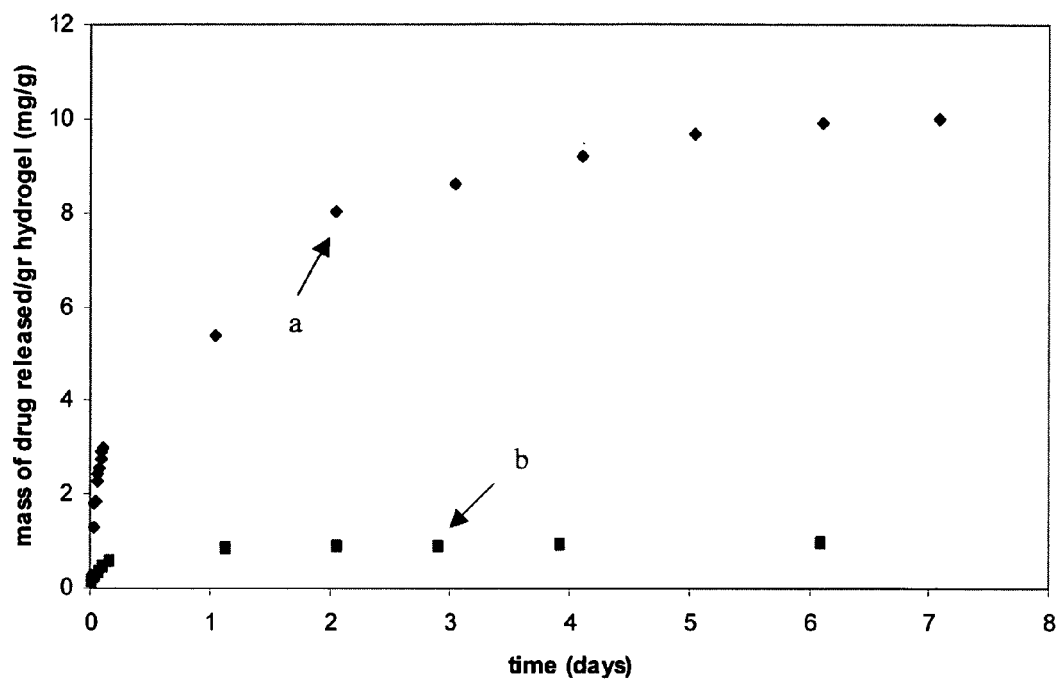
Figure 7: Comparision of long term release rates from hydrogels prepared by: a) directly dissolving Lidocaine in polymerization mixture; b) dissolving Lidocaine molecules in the oil phase of Type 4 microemulsion with 3% oil

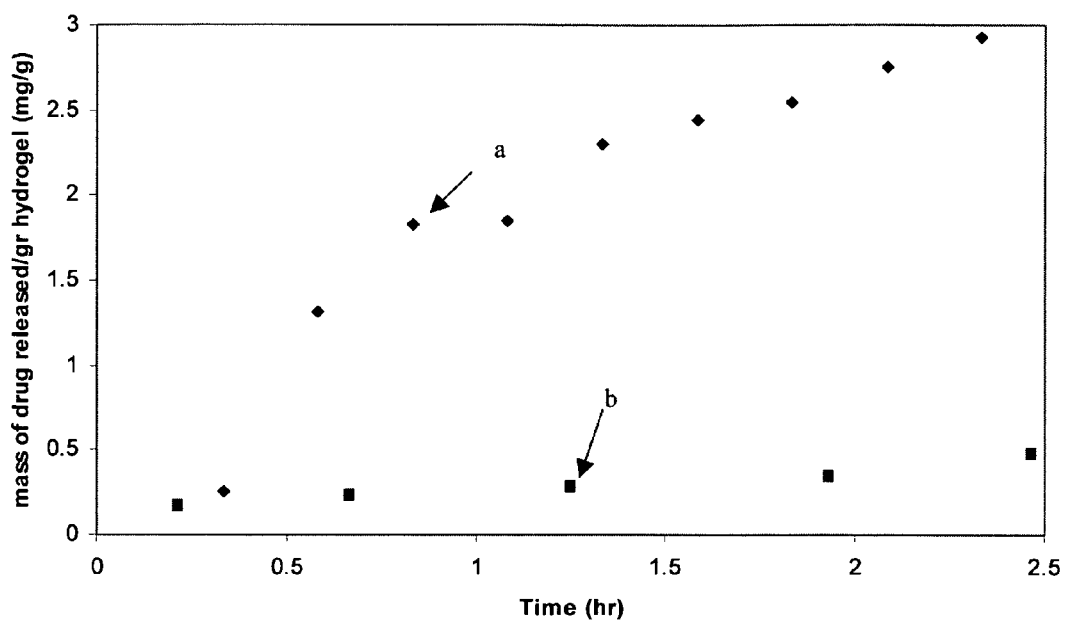
Figure 8: Comparision of short term release rates from hydrogels prepared by: a) directly dissolving Lidocaine in polymerization mixture; b) dissolving Lidocaine molecules in the oil phase of Type 4 microemulsion

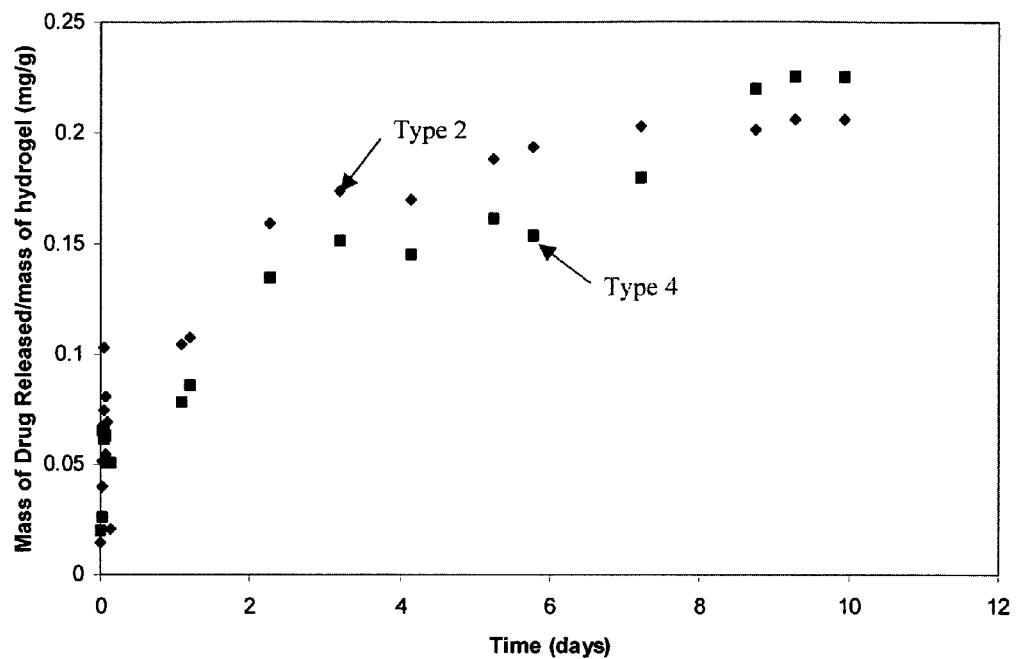
Figure 9: Drug diffusion from hydrogels loaded with Type 2 and Type 4 microemulsions. Both hydrogels contain the same drug concentration of 0.22 mg Lidocaine (oil soluble form)/gr of hydrogel.

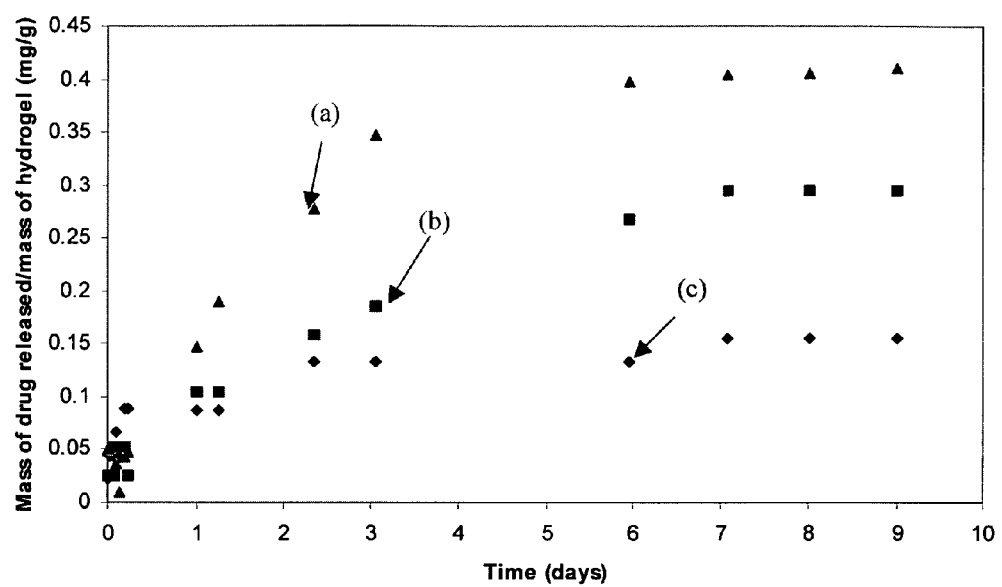
Figure 10: Drug release from a Type 3 hydrogel loaded with (a) 0.42 mg (b) 0.3 mg (c) 0.17 mg lidocaine (oil soluble form)/gr hydrogel

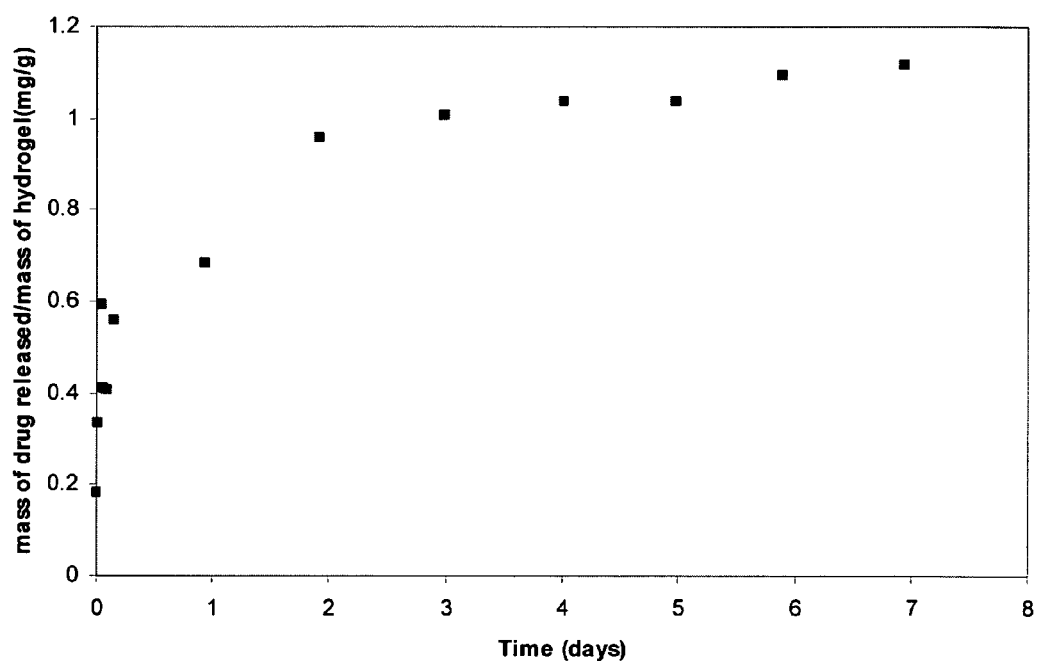
Figure 11: Drug release by liposome laden contact lens

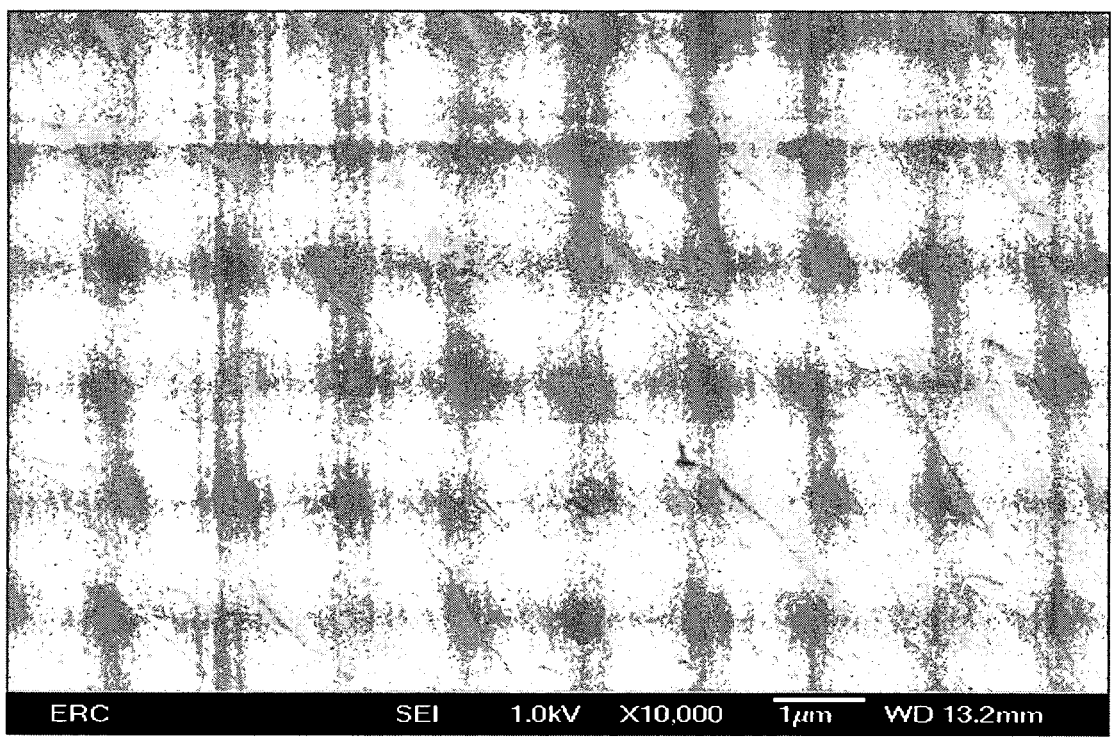
Figure 12: SEM image of a pure p-HEMA hydrogel

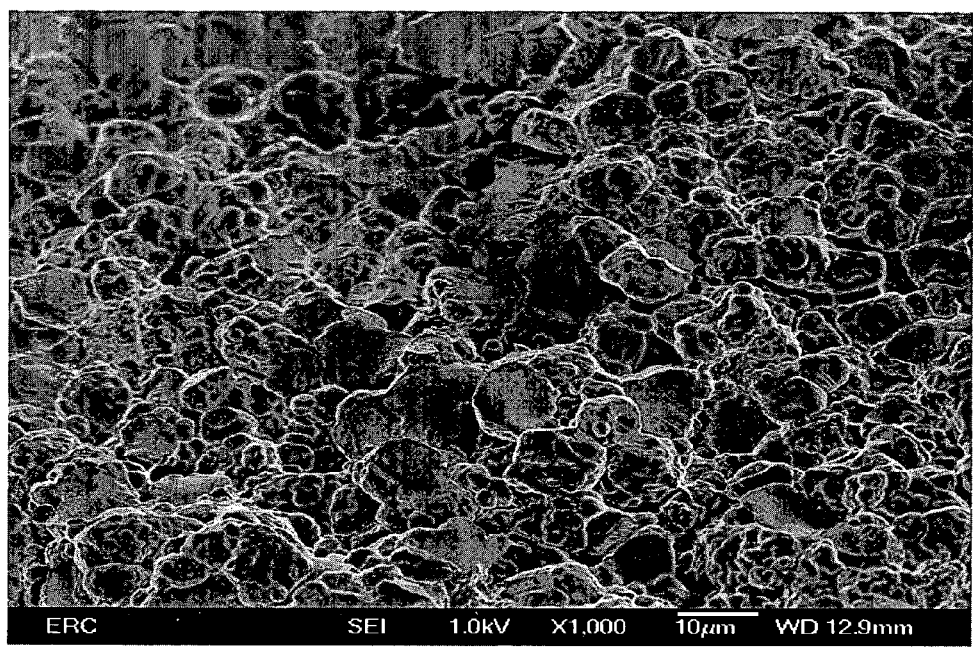
Figure 13: SEM image of a hydrogel loaded with drug-laden particles of Type 1 microemulsion

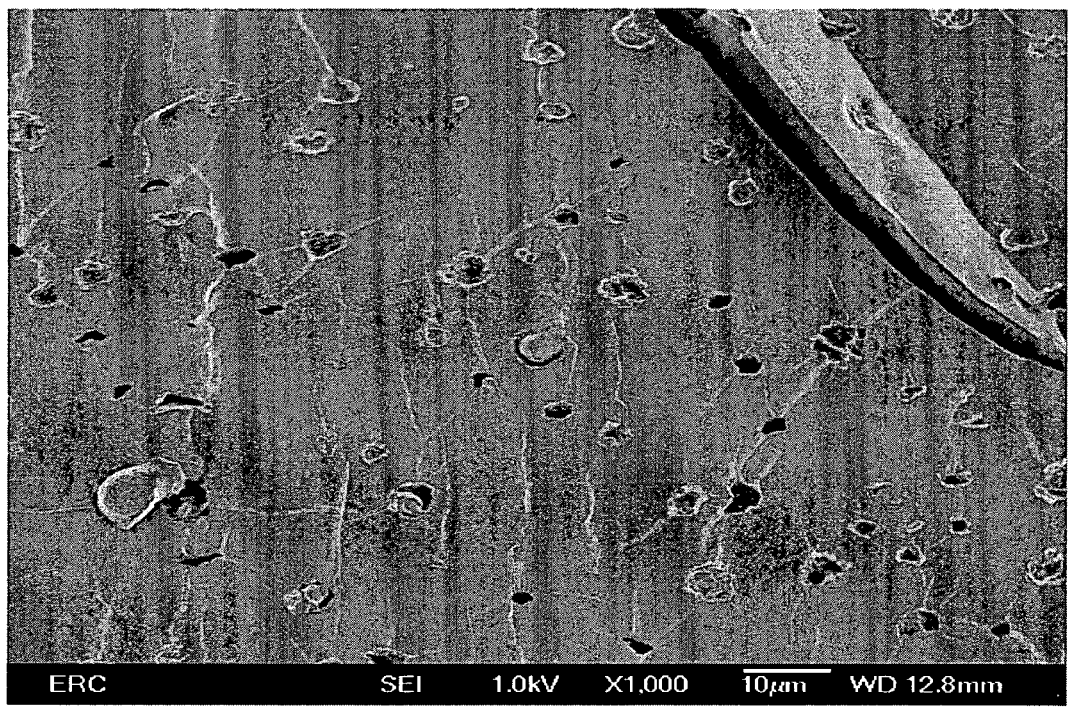
Figure 14: SEM image of a hydrogel loaded with drug-laden particles of Type 2 microemulsion

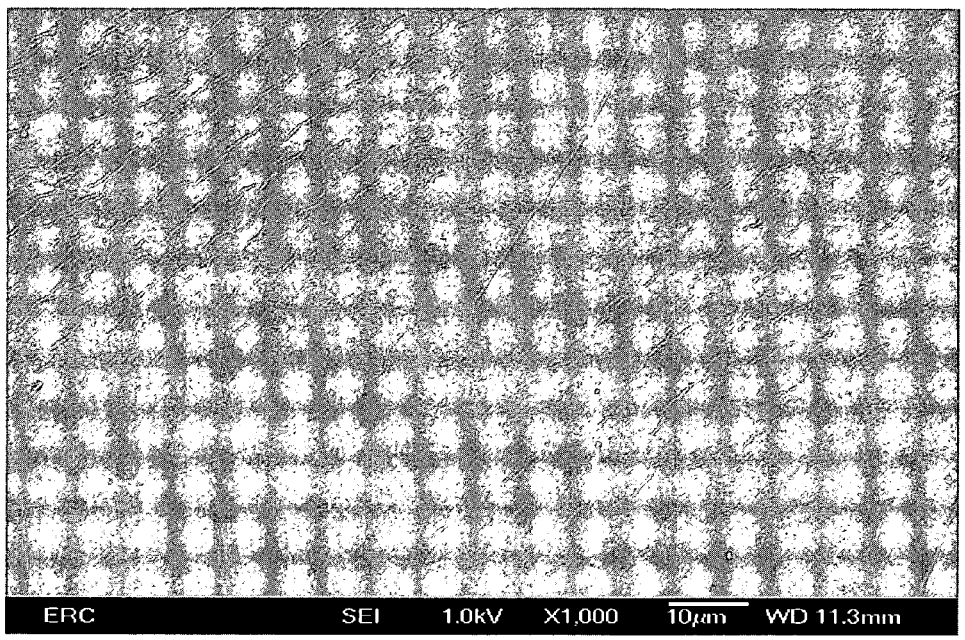
Figure 15: SEM image of a hydrogel loaded with drug-laden particles of Type 3 microemulsion

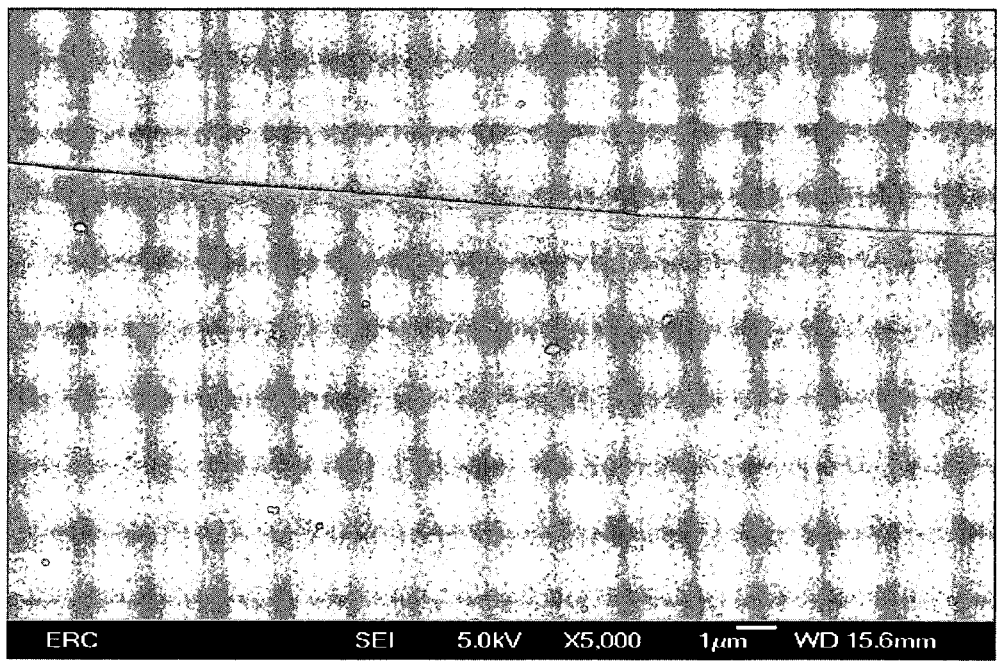
Figure 16: SEM image of a hydrogel loaded with drug-laden particles of Type 4 microemulsion

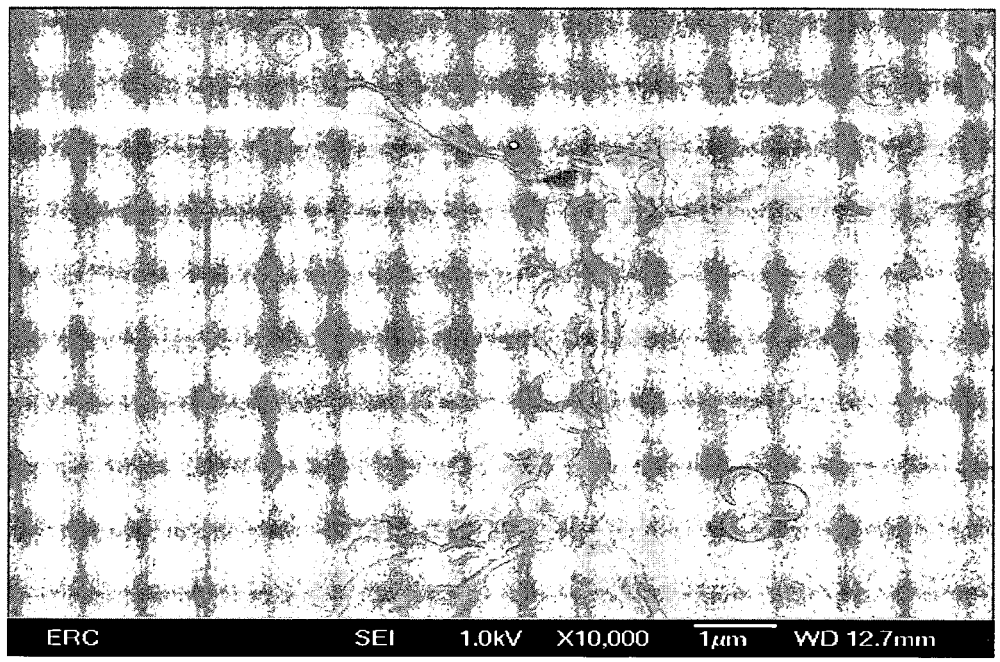
Figure 17: SEM image of a hydrogel loaded with drug-laden particles of Type1 microemulsion at a higher magnification showing the particles

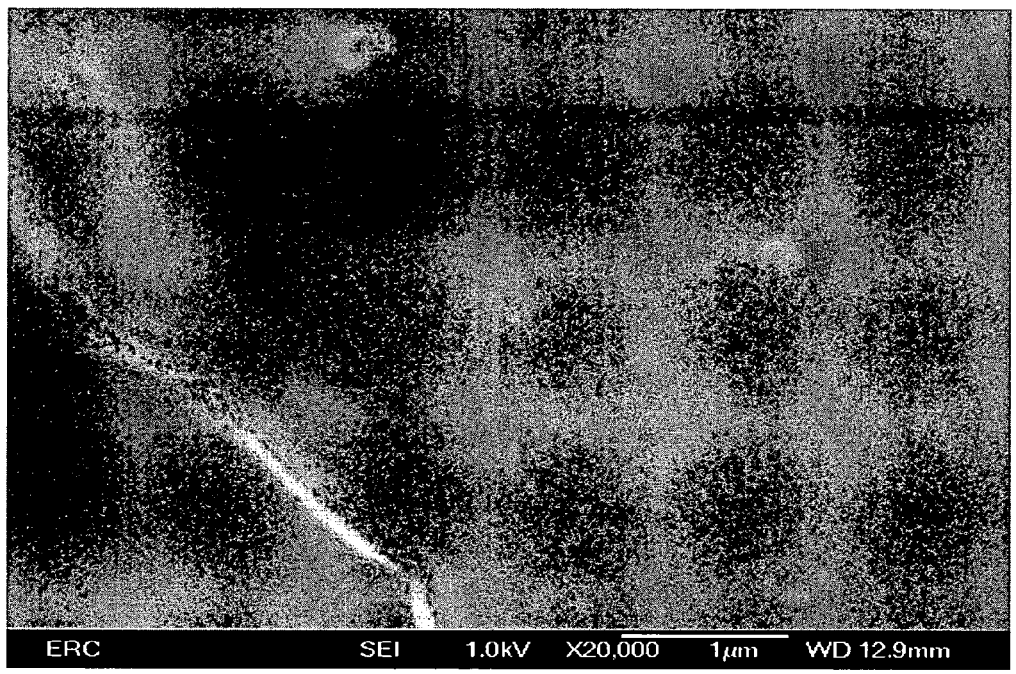
Figure 18: SEM image of a hydrogel loaded with drug-laden particles of Type 2 microemulsion at a higher magnification showing the particles

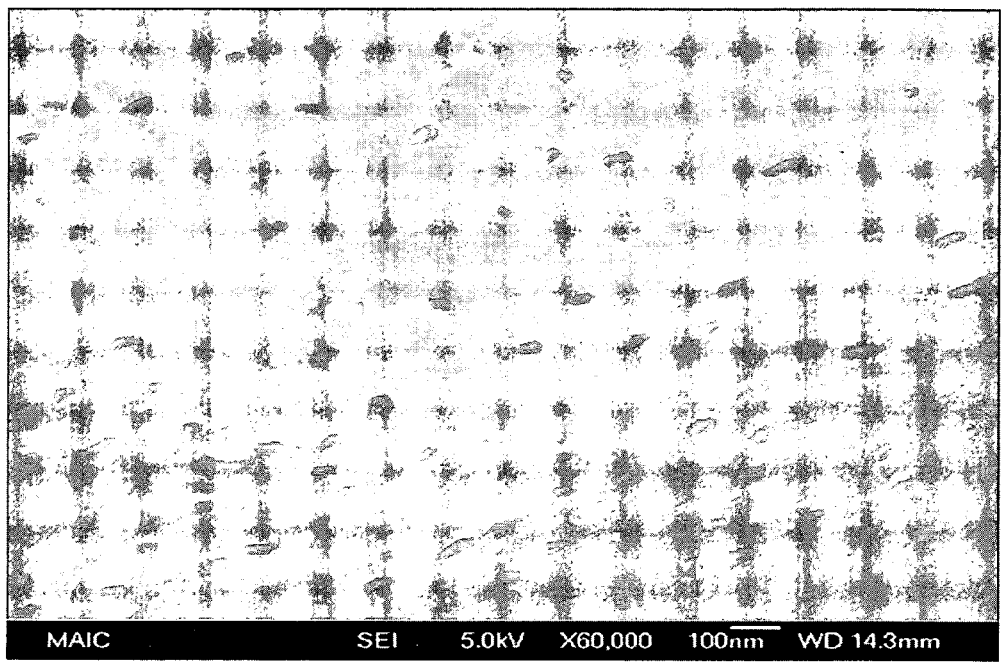
Figure 19: SEM image of a hydrogel loaded with drug-laden particles of Type 4 microemulsion at a higher magnification showing the particles

OPHTHALMIC DRUG DELIVERY SYSTEM

FIELD OF THE INVENTION

This is a continuation-in-part application of application Ser. No. 10/454,836 filed Jun. 5, 2003. Reference is hereby made to provisional patent application Ser. No. 60/385,571 filed Jun. 5, 2002, the benefit of the filing date of which is claimed herein. The present invention relates to methods and systems for the delivery of ophthalmic drugs to the eye.

BACKGROUND OF THE INVENTION

Description of the Prior Art

Providing and maintaining adequate concentration of drugs in the pre-corneal tear film for extended periods of time is one of the major problems plaguing methods and systems for ocular drug delivery. When they are applied as eye drops, most drugs penetrate poorly through the cornea. Drainage of instilled drug with the tear fluid, and absorption through the conjunctiva leads to a short duration of action. The additional pre-corneal factors that contribute to the poor ocular bio-availability of many drugs when instilled in the eye as drops are tear turnover and drug binding to tear fluid proteins. In addition to the above factors, the rate of corneal uptake is high at early times, but it declines rapidly. This may lead to a transient period of overdose and associated risk of side effects followed by an extended period of sub-therapeutic levels before the administration of next dose. All the above factors indicate the need for an ocular drug delivery system that will be as convenient as a drop but will serve as a controlled release vehicle [Nagarsenker, M. S., Londhe, V. Y., Nadkarni, G. D., "*Preparation and evaluation of liposomal formulations of tropicamide for ocular delivery*", Int. J. of Pharm., 1990, 190: 63-71].

Topical delivery via eye drops that accounts for about 90% of all ophthalmic formulations is very inefficient and in some instances leads to serious side effects [Bourlais, C. L., Acar, L., Zia H., Sado, P. A., Needham, T., Leverge, R., "*Ophthalmic drug delivery systems*", Progress in retinal and eye research, 1998, 17, 1: 33-58]. Only about 5% of the drug applied as drops penetrate through the cornea and reaches the ocular tissue, while the rest is lost due to tear drainage [Lang, J. C., "*Ocular drug delivery conventional ocular formulations*". Adv. Drug Delivery, 1995, 16: 39-43]. The drug mixes with the fluid present in the tear film upon instillation and has a short residence time of about 2-5 minutes in the film. About 5% of the drug gets absorbed and the remaining flows through the upper and the lower canaliculi into the lacrimal sac. The drug containing tear fluid is carried from the lacrimal sac into the nasolacrimal duct, and eventually, the drug gets absorbed into the bloodstream. This absorption leads to drug wastage and more importantly, the presence of certain drugs in the bloodstream leads to undesirable side effects. For example, beta-blockers such as Timolol that is used in the treatment of wide-angle glaucoma have a deleterious effect on heart [TIMPOTIC® prescribing information, supplied by MERCK]. Furthermore, application of ophthalmic drugs as drops results in a rapid variation in drug delivery rates to the cornea that limits the efficacy of therapeutic systems [Segal, M., "*Patches, pumps and timed release*", FDA *Consumer* magazine, October 1991]. Thus, there is a need for new ophthalmic drug delivery systems that increase the residence time of the drug in the eye, thereby reducing wastage and eliminating side effects.

There have been a number of attempts in the past to use contact lenses for ophthalmic drug delivery; however, all of these focused on soaking the lens in drug solution followed by insertion into the eye. In one of the studies, the authors focused on soaking the lens in eye-drop solutions for one hour followed by lens insertion in the eye [Hehl, E. M., Beck, R., Luthard K., Guthoff R., "*Improved penetration of aminoglycosides and fluoroquinolones into the aqueous humour of patients by means of Acuvue contact lenses*", European Journal of Clinical Pharmacology, 1999, 55 (4): 317-323]. Five different drugs were studied and it was concluded that the amount of drug released by the lenses are lower or of the same order of magnitude as the drug released by eye drops. This happened perhaps because the maximum drug concentration obtained in the lens matrix is limited to the equilibrium concentration. In another study researchers developed a contact lens with a hollow cavity by bonding together two separate pieces of lens material [Nakada, K., Sugiyama, A., "Process for producing controlled drug-release contact lens, and controlled drug-release contact lens thereby produced"; U.S. Pat. No. 6,027,745, May 29, 1998]. The compound lens is soaked in the drug solution. The lens imbibes the drug solution and slowly releases it upon insertion in the eye. The compound lens suffers from the same limitations as the drug-soaked lens because the concentration of the drug in the cavity is the same as the concentration of the drug in the drops and thus such a lens can supply the drug for a limited amount of time. Furthermore, the presence of two separate sheets of lens material leads to smaller oxygen and carbon dioxide permeabilities that can cause an edema in the corneal tissue. The other studies and patents listed below suffer from the same limitations because they are also based on soaking of contact lenses or similar devices in drug-solutions followed by insertion into the eye [Hillman, J. S., "Management of acute glaucoma with Pilocarpine-soaked hydrophilic lens" Brit. J. Ophthal. 58 (1974) p. 674-679, Ramer, R. and Gasset, A., "Ocular Penetration of Pilocarpine:" Ann. Ophthalmol. 6, (1974) p. 1325-1327, Montague, R. and Wakins, R., "Pilocarpine dispensation for the soft hydrophilic contact lens" Brit. J. Ophthal. 59, (1975) p. 455-458, Hillman, J., Masters, J. and Broad, A. "Pilocarpine delivery by hydrophilic lens in the management of acute glaucoma" Trans. Ophthal. Soc. U.K. (1975) p. 79-84, Giambattista, B., Virno, M., Pecori-Giraldi, Pellegrino, N. and Motolese, E. "Possibility of Isoproterenol Therapy with Soft Contact Lenses: Ocular Hypotension Without Systemic Effects" Ann. Ophthalmol 8 (1976) p. 819-829, Marmion, V. J. and Yardakul, S. "Pilocarpine administration by contact lens" Trans. Ophthal. Soc. U.K. 97, (1977) p. 162-3, U.S. Pat. No. 6,410,045, Drug delivery system for antiglaucomatous medication, Schultz; Clyde Lewis, Mint; Janet M; U.S. Pat. No. 4,484,922, Occular device, Rosenwald; Peter L., U.S. Pat. No. 5,723,131, Contact lens containing a leachable absorbed material, Schultz; Clyde L. Nunez; Ivan M.; Silor; David L.; Neil; Michele L.].

A number of researchers have trapped proteins, cells and drugs in hydrogel matrices by polymerizing the monomers that comprise the hydrogel, in presence of the encapsulated species [Elisseeff, J., McIntosh, W., Anseth, K., Riley, S., Ragan, P., Langer, R., "*Photoencapsulation of chondrocytes in poly(ethylene oxide)-based semi-interpenetrating networks*", Journal of Biomedical Materials Research, 2000, 51 (2): 164-171; Ward, J. H., Peppas, N. A., "*Preparation of controlled release systems by free-radical UV polymerizations in the presence of a drug*", Journal of Controlled Release, 2001, 71 (2): 183-192; Scott, R. A., Peppas, N. A., "*Highly crosslinked, PEG-containing copolymers for sustained solute delivery*", Biomaterials, 1999, 20 (15): 1371-

1380; Podual, K., Doyle F. J., Peppas N. A., "*Preparation and dynamic response of cationic copolymer hydrogels containing glucose oxidase*", Polymer, 2000, 41 (11): 3975-3983; Colombo, P., Bettini, R., Peppas, N. A., "*Observation of swelling process and diffusion front position during swelling in hydroxypropyl methyl cellulose (HPMC) matrices containing a soluble drug*", Journal of Controlled Release, 1999, 61 (1,2): 83-91; Ende, M. T. A., Peppas, N. A., "*Transport of ionizable drugs and proteins in crosslinked poly(acrylic acid) and poly(acrylic acid-co-2-hydroxyethyl methacrylate) hydrogels. 2. Diffusion and release studies*", Journal of Controlled Release, 1997, 48 (1): 47-56; U.S. Pat. No. 4,668,506]. There are two main advantages of our proposed method of entrapment of drug in nanoparticles over soaking and direct entrapment of drug in a gel. First, if the solute is directly trapped in the gel, the release rates are controlled by diffusion through the gel. Contact lenses have to be very thin (about 100 μm thick) and only lightly crosslinked to ensure high oxygen permeability. Thus, if drugs are directly trapped in the lens during polymerization, they will be released in a short period of time. If the drugs are trapped inside the nanoparticles, and if the nanoparticles are designed to release drugs slowly, then a contact lens loaded with the drug containing particles can release drug for longer periods of time. Secondly, since the solubility of the hydrophobic drugs is much higher in oil, a significantly higher drug loading can be achieved by entrapping the drug in oil filled nanoparticles or nanocapsules, and subsequently, dispersing these particles in a hydrogel matrix. Recently, Graziacascone et al [Graziacascone, M., Zhu, Z., Borselli, F., Lazzeri, L., "*Poly(vinyl alcohol) hydrogels as hydrophilic matrices for the release of lipophilic drugs loaded in PLGA nanoparticles*", Journal of Material Science: Materials in Medicine, 2002, 13: 29-32] published a study on encapsulating lipophilic drugs inside nanoparticles, and entrapping the particles in hydrogels. They used PVA hydrogels as hydrophilic matrices for the release of lipophilic drugs loaded in PLGA particles. However, there is no study available in literature that focuses on incorporating drug-laden nanoparticles in hydrogels in a manner such that the gel stays transparent and can be used for ophthalmic drug delivery.

SUMMARY OF THE INVENTION

One embodiment of the invention relates to a drug delivery system comprising a contact lens having dispersed therein as nanoparticles, an ophthalmic drug nanoencapsulated in a material from which the ophthalmic drug is capable of diffusion into and migration through the contact lens and into the post-lens tear film when the contact lens is placed on the eye. The particle size of the nanoparticles and the number thereof dispersed in the contact lens are such that the contact lens remains substantially transparent.

A second embodiment of the invention is a method of administering an ophthalmic drug to a patient in need thereof comprising placing on the eye thereof the above described drug delivery system.

Third and fourth embodiments of the invention concern a kit and its use for the storage and delivery of ophthalmic drugs to the eye, the kit comprising:
a) a first component containing at least one of the above described drug delivery systems, and
b) a second component containing at least one storage container for the first component, the storage container additionally containing a material that substantially prevents the diffusion and migration of the ophthalmic drug during storage.

A fifth embodiment of the invention relates to a method of preparing the drug delivery system of claim 1 comprising:
c) providing the nanoencapsulated ophthalmic drug, and
d) preparing the contact lens from materials that incorporate the nanoencapsulated ophthalmic drug, such that the nanoencapsulated ophthalmic drug is substantially uniformly dispersed throughout the contact lens.

Sixth and seventh embodiments of the invention concern articles of manufacture comprising packaging material and the above described ophthalmic drug delivery system or the above-described kit contained within the packaging material, wherein the packaging material comprises a label which indicates that the ophthalmic drug delivery system and kit can be used for ameliorating symptoms associated with pathologic conditions of the eye.

BRIEF DESCRIPTION OF THE DRAWINGS

FIG. 1 is a schematic view of the novel particle laden lens of the invention inserted in the eye.

FIGS. 2-5 are particle size distributions for various microemulsions.

FIG. 6 is transmittance values of various hydrogels.

FIGS. 7-11 are comparisons of release rates of a drug from various hydrogels.

FIGS. 12-19 are SEM photographs of various drug-laden hydrogels.

DETAILED DESCRIPTION OF THE INVENTION

The present invention is predicated on the discovery that contact lenses, preferably, soft contact lenses can function as new vehicles for ophthalmic drug delivery to reduce drug loss, eliminate systemic side effects, and improve drug efficacy. The crux of the invention resides in the encapsulation of the ophthalmic drug formulations in nanoparticles and the dispersion of these drug-laden nanoparticles in the contact lens matrix (FIG. 1). If the nanoparticle size and loading are sufficiently low, the particle-loaded lens is transparent. The limiting size of the drug-laden nanoparticles is ultimately dependent on the refractive index thereof, but generally is less than about 50 nm to 200 nm. The invention is exemplified herein using soft hydrogel lenses that are made of poly 2-hydroxyethyl methacrylate p-(HEMA). However, it will be understood by those skilled in the art that the range of materials that may be employed as vehicles in the present invention is limited only by the selection of materials that may be employed in the manufacture of contact lenses and the nature of the particular ophthalmic drug to be incorporated therein. The term, "optically transparent" as used herein is intended to refer to a degree of transparency equivalent to that of p-HEMA or other material employed as a contact lens. The p-HEMA hydrogel matrix may be synthesized by any convenient method, e.g., bulk or solution free radical polymerization of HEMA monomers in presence of a cross linker such as ethylene glycol-di-methacrylate (EGDMA) [Mandell, R. B., "*Contact Lens Practice: Hard and Flexible Lenses*", $2^{nd}$ ed., Charles C. Thomas, Springfield, vol. 3, 1974].

Addition of drug-laden particles to the polymerizing medium results in the formation of a particle-dispersion in the hydrogel matrix. If contact lenses made of this material are placed on the eye, the drug molecules will diffuse from the particles, travel through the lens matrix, and enter the post-lens tear film (POLTF), i.e., the thin tear film trapped in between the cornea and the lens. In the presence of the lens, drug molecules will have a much longer residence time in the post-lens tear film, compared to about 2-5 minutes in the case of topical application as drops [Bourlais, C. L., Acar, L., Zia H., Sado, P. A., Needham, T., Leverge, R., "*Ophthalmic drug delivery systems*", Progress in retinal and eye research, 1998, 17, 1: 33-58; Creech, J. L., Chauhan, A., Radke, C. J., "*Dispersive mixing in the posterior tear film under a soft contact lens*", I&EC Research, 2001, 40: 3015-3026; McNamara, N. A., Polse, K. A., Brand, R. D., Graham, A. D., Chan, J. S., McKenney, C. D., "*Tear mixing under a soft contact lens: Effects of lens diameter*". Am. J. of Ophth., 1999, 127(6): 659-65]. The longer residence time will result in a higher drug flux through the cornea and reduce the drug inflow into the nasolacrimal sac, thus reducing drug absorption into the blood stream. In addition, due to the slow diffusion of the drug molecules through the particles, drug-laden contact lenses can provide continuous drug release for extended periods of time.

In the examples below we demonstrate dispersion of two types of drug laden nanoparticles in hydrogels: microemulsion drops and liposomes. Microemulsions are thermodynamically stable isotropic dispersions of nano-size drops in water stabilized by surfactants. An oil-water (O/W) microemulsion is an effective vehicle for encapsulating a hydrophobic drug due to its ability to dissolve the drug in the oil phase. It is also preferred to employ microemulsion drops as drug reservoirs because of the flexibility in stabilizing the particles and controlling the kinetics of drug release from the particles by manipulating the surface characteristics of the nano-sized oil drops. For instance, one could stabilize the particles to prevent aggregation and slow down the drug release from the drops by depositing a thin partial-layer of silica on the surface [Arriagada, F. J., Osseo-Asare, K., "*Synthesis of nanosize silica in a nonionic water-in-oil microemulsion: effects of the water/surfactant molar ratio and ammonia concentration*", Journal of Colloid & Interface Science 1999, 211: 210-220]. Liposomes are essentially lipid bilayers that fold to form spherical vesicles. Liposomes have a hydrophilic core and a hydrophobic annulus. One could also utilize a number of other types of nanoparticles for encapsulating drugs such as 1 Chitosan nanoparticles (CS)
2 Human Serum Albumin nanoparticles
3 Biodegradable poly(alkylcynoacrylates), e.g., polybutylcyanoacrylate, polyhexylcyanoacrylate, polyethylcyanoacrylate (PECA), (polyisobutylcyanoacrylate), polycyanoacrylate (PCA), and the like.
4 Silica nanospheres
5 PEG'ylated core-shell nanoparticles
6 Biodegradable PLGA (poly(D,L-lactide-co-glycolide)) particles PLA (polu lactic acid), PGA, PLG (poly(D,L-glycolide))polymeric nanoparticles
7 Microemulsion nanodroplets
8 Liposomes
9 Biocompatible gliadin nanoparticles
10 Low pH sensitive PEG stabilized plasmid-lipid nanoparticles
11 Biodegradable calcium phosphate NP (CAP)
12 Legumin (a storage protein found in pea seeds)
13 Tocopherol derivatives stabilized nano-sized emulsion particles
14 Polysaccharides grafted with Polyesthers (amphyphilic copolymers)
15 PLA-PEG nanoparticles
16 Nanoparticles composed of hydrophilic proteins coupled with a polipoprotein E
17 Biodegradable poly(.vepsiln-caprolactone) nanoparticles
18 poly(methylidene malonate)
19 gelatin
20 poly(E-caprolactone)
21 sodium alginate
22 agarose hydrogel NP
23 PMMA NP
24 biotinylated poly(ethylene glycol) conjugated with lactobionic acid (BEL)
25 carboxylmethyl dextran magnetic NP (CMD MNPS)
26 poly(vinyl alcohol) hydrogel NP
27 biotinylated pullulan acetate (BPA)
28 diblock copolymers It will further be understood by those skilled in the art that the term, "encapsulation", as used herein refers to the complete enclosure of the ophthalmic drug by the "encapsulation" material as well as deposition of the ophthalmic drug on the encapsulation material particles. Furthermore, the particles can be replaced by nanodomains of polymers that can solubilize the drugs. The nanodomains could be formed either by dispersing the insoluble polymer in the hydrogel matrix or by incorporating the insoluble polymer in the hydrogel chains. For example if a section of PMMA is incorporated in p-HEMA, this section will fold in a water-like environment to form nanoparticles that can solubilize more hydrophobic drugs. Also the type of particles that can be utilized depends on the drug that needs to be incorporated in the lens. For example microemulsion drops are not useful for trapping hydrophilic drugs; Liposomes are appropriate for this application.

Four kinds of microemulsions and liposomes were used in the examples below. The microemulsions are referred to as Type 1, Type 2, Type 3 and Type 4 microemulsions. Type 1 microemulsions consist of droplets of canola oil dispersed in 2% NaCl solution stabilized by Panodan SDK and Tween 80 surfactants. Type 2 microemulsions employ the same materials as Type 1. In addition, octadecyl-tri-methoxy silane (OTMS) and dilute HCL solution are used in the formulation of Type 2 microemulsion. Type 3 microemulsions are O/W microemulsions of Hexadecane in Water stabilized by Brij 97 surfactant. Distilled water is used as the continuous phase. Type 4 microemulsions comprise of oil drops with an annulus of silica dispersed in water. It is synthesized with OTMS, dilute HCl and the materials used in Type 3 microemulsions.

The synthesis procedure for the Type 1 microemulsion is as follows: dissolve 4 g of Tween 80 in 10 g of 2% NaCl solution with continuous heating and stirring to form a 40% w/w solution. Separately, prepare 2.5 g of a solution of Canola oil and Panodan SDK in a 1.5:1.0 w/w ratio. Mix the two solutions, and heat and stir the resulting milky solution at approximately 100° C. until it becomes clear, indicating microemulsion formation. Type 1 microemulsions are light yellow in color; however, it is transparent when freshly prepared and can be used in contact lens applications. After 3 days of shelf storage, the microemulsion starts to slowly loose its transparency and becomes a milky solution due to particle agglomeration.

Type 2 microemulsions comprise of oil drops with an annulus of silica dispersed in water. Synthesis of this microemulsion is performed by adding 40 mg of OTMS to 12 g of Type 1 mixture and allowing the microemulsion to form at the same conditions as those in formulation of Type 1. Since OTMS is an amphyphilic molecule, it is expected to accumulate at the drop surface during emulsification. As soon as the microemulsion is formed, add 1.17 g of 1N HCl solution for each gram of microemulsion. Addition of HCl results in hydrolysis of OTMS followed by condensation on the surface of the oil drops. Hydrolysis reaction is performed in the same conditions as the microemulsion formation in a water bath for 6 hours. Hydrolysis and condensation of OTMS leads to formation of silica shell surrounding the oil drop. The resulting solution is transparent and has a slight yellowish color. It is stable after about 2 weeks of shelf storage.

To synthesize Type 3 microemulsions, dissolve approximately 0.12 g of hexadecane in 10 g water and add 1.5 g of Brij 97 to stabilize the mixture. Heat the mixture of oil, water and surfactants at 60° C. and simultaneously stir at 1000 rpm until the solution becomes clear. The amount of hexadecane used in the microemulsion is much less than the maximum amount that can be dissolved without destabilizing the microemulsion. The resulting microemulsion is a colorless, transparent solution with an average particle size of 10 nm. It remains stable after 2 weeks of shelf storage. This microemulsion is called Type 2 in the following discussion.

Synthesis procedure for Type 4 microemulsion is as follows: add 40 mg of OTMS to 12 g of Type 3 mixture and allow the microemulsion to form at the same conditions as those in formulation Type 3. OTMS is expected to accumulate at the drop surface during emulsification as in Type 2 microemulsions. As soon as the microemulsion is formed, add 1.17 g of 1N HCl solution for each gram of microemulsion. Hydrolysis reaction is performed at the same conditions as the microemulsion formation in a water bath for 6 hours. Hydrolysis and condensation of OTMS leads to formation of a silica core surrounding the oil drop. The resulting solution is transparent and colorless with a mean particle size of about 15 nm.

To synthesize liposomes, DMPC and drug are dissolved in a 9:1 chloroform/ethyl alcohol mixture. Nitrogen is bubbled through the mixture to evaporate the solvents and obtain an even and uniform dried film. The dried lipid layer is dispersed in 0.5 ml water and sonicated in an ultrasonic cleaner (Laboratory Supplies Co. Inc. Model: G112SP1) for 20 minutes. Next, the solution is diluted with 4.5 ml of water and transferred into a probe sonicator (Fisher Scientific sonic dismembrator, model 100). The solution is further sonicated for 40 minutes with the probe sonicator to produce small liposomes (80 nm) which are called small unilamellar vesicles (SUV).

P-HEMA hydrogels are synthesized by free radical solution polymerization of HEMA monomer. To polymerize the hydrogel, dissolve 40 mg of EGDMA in 10 g of HEMA and mix the resulting solution with distilled water in a 2:3 w/w ratio. Degas the resulting solution by bubbling nitrogen through the solution for 30 minutes to eliminate the dissolved oxygen. Add 25 mg of AIBN to 25 g of the polymerization mixture and pour it between two glass plates covered by a thin layer of silicone oil or plastic to prevent sticking of the gel with the glass. The two glass plates are separated from each other with a 1 mm Teflon tubing. Polymerization is performed in an oven at 60° C. for 24 hr. The hydrogel film is subsequently soaked in water. In order to synthesize the drug-loaded hydrogel, water in the formulation described above is simply replaced by an aqueous solution containing drug-loaded particles.

Drug release studies from the hydrogels loaded with microemulsion drops containing a drug called Lidocaine were conducted. An oil soluble form of Lidocaine was obtained by reacting the water-soluble form with NaOH. We dissolve both NaOH and water-soluble form of Lidocaine in water in small test tubes and mix the two solutions. At basic pH Lidocaine precipitates out of the solution. The precipitated form which is the oil soluble form was extracted from the water by adding hexane in the solution. The addition of hexane leads to a two-phase mixture. The upper, drug containing, hexane phase is removed with a pipette and heated to evaporate the hexane leaving a white, solid residue of oil soluble Lidocaine.

The drug release experiment consists of suspending the drug-loaded hydrogel in a well-stirred beaker containing a known volume of water. Aliquots of water are withdrawn at various times and concentration of the drug is measured. Hydrogels that contain microemulsion particles but do not contain any drug were also prepared and designated as blanks. The same measurements of these blanks were taken as the ones with drug particles and used as references to calculate the amount of drug release. UV-Vis spectroscopy was employed to determine the drug concentration with respect to time. To relate absorbance values obtained from the spectrometer to the drug concentration, calibration curves for the oil soluble form of lidocaine in water were prepared. Drug release experiments were conducted at 270 nm wavelength and the percentage of the drug released into the water was calculated using the calibration curves.

Microemulsions were characterized by light scattering (Brookhaven Instruments, Zeta Plus particle size analyzer) to determine the particle size. All samples were filtered with a 0.2 μm syringe filter before sizing.

The transparency of hydrogels were determined by light transmittance studies (Thermospectronic Genesys 10 UV-Vis spectrometer at a visible wavelength of light (600 nm)). Dry hydrogel samples that fit the sampling cell were prepared and attached into a plastic cuvet. The transmittance values of each hydrogel sample were measured by taking the transmittance of the plastic cuvet as blank.

A TJEOL JSM6330F Field Emission Scanning Electron Microscope was employed to characterize the structure of the drug-laden hydrogels. The hydrogel samples were cracked under liquid nitrogen and the SEM images were obtained of the freshly exposed surface. The samples are vacuum dried before mounting on the sampler to remove any remaining water or the oil in order not to damage the instrument. Samples are kept in a vacuum oven overnight for this purpose. The optical microscope (Olympus BX60 Optical with SPOT RT Digital Camera) images of the samples taken both before and after the vacuum treatment are used to determine any possible structure changes that may occur due to vacuum drying. The lowest possible accelerating voltages were used and a very thin Carbon coating was applied to prevent charging. Magnifications as high as 80 kX were obtained.

Drug diffusion studies were also performed in a Thermospectronic Genesys 10 UV-Vis spectrometer at UV range as explained above.

Synthesis and Transmittance Studies with Hydrogels Loaded with Drug Laden Microemulsion Nano-Droplets As explained above, soaking the contact lens in a drug solution to load the hydrogel with the drug solution and subsequently releasing it is not very useful. Another possible solution would be to dissolve the drug molecules directly in the polymerization mixture and perform the polymerization with drug molecules in the hydrogel matrix. However, there are several drawbacks to this application. First, most of the ophthalmic drug formulations that are used in the eye treatment are hydrophobic molecules. This property of the drug molecules makes it hard for them to dissolve in the water phase of the polymerization mixture. HEMA molecule has some hydrophobicity, however most of the time it is not sufficiently high to dissolve enough drug molecules to release drug for extended periods of time. Also, the only resistance for the diffusion of drugs from the hydrogel to the eye is diffusion of these particles from the lens matrix into the eye and this leads to a very fast release that is not desirable.

Additionally, one has no control over the drug release rates in this case; the drug molecule travels through the hydrogel matrix with natural diffusion. Another very important disadvantage of directly dissolving the drug molecules in the polymerization mixture is the possibility that drug molecules may become involved in the polymerization reaction and lose their functionality. All of the above disadvantages make it impossible to dissolve drug molecules directly in the polymerization mixture. The crux of the present invention is to provide a capsule that will entrap the drug molecules instead of directly dissolving them in the hydrogel matrix. In this way, one can prevent the interaction of drug molecules with the polymerization mixture. Also one will be able to dissolve more drug by choosing an appropriate hydrophobic liquid to dissolve it. Then this hydrophobic liquid phase saturated with drug is entrapped in a nanoparticle. This prevents both the interaction of drug molecules with the polymerization mixture and also provides additional resistance to drug release; i.e., the drug must first diffuse through the oil phase to reach to the particle surface and then has to penetrate the particle surface to reach the hydrogel matrix. By changing the properties of the nanoparticles or modifying their mobility and stability one can achieve good control over the rate of drug release and have the potential to obtain zero order drug release rates.

As explained above, Type 1 is a Windsor 1 type O/W microemulsion formulation. This formulation was chosen because of its biocompatible nature and ability to dissolve comparably higher amounts of drug in the oil phase. The microemulsion contains about 10% of oil, which is comparably higher than the similar biocompatible O/W microemulsions. This allows one to increase the concentration of the drug inside the hydrogel to the desired therapeutic levels. Type 1 microemulsion is yellowish yet transparent, which is suitable for contact lens applications. Light scattering studies (FIG. 2) showed that this microemulsion has a droplet size of approximately 14 nm that is small enough to obtain a transparent microemulsion. The Type 1 microemulsion is then used in the hydrogel formulation as the water phase. The hydrogels synthesized this way contain drug dissolved inside the oil droplets in a continuous medium of water. When the microemulsion is added into the polymerization mixture containing monomer, initiator and cross-linker, the solution became completely opaque. One possible reason for this could be the interaction of surfactant molecules with the HEMA monomer (surfactant Tween 80 is soluble in monomer). Resulting hydrogels prepared with Type 1 microemulsion are, therefore, not transparent. Transmittance of these hydrogels is about 4.4% whereas the values for the pure p-HEMA hydrogels are around 87% at this concentration of the water phase (see FIG. 6). Note that these transmittance values are for lenses ten times thicker than a typical contact lens.

Therefore, it was concluded that it was needed to prevent the interaction of surfactant molecules with the monomer. For this purpose, a silica shell was formed around the surfactant molecules surrounding the oil droplets. In this way one would be able to stabilize the oil droplets and prevent the interaction of surfactants with the monomer. Octadecyl-tri-methoxysilane (OTMS) was added to the Type 1 microemulsion and allowed to polymerize in a weak acidic medium. The resulting microemulsion was yellowish and transparent. Light scattering studies (FIG. 3) showed that the microemulsion has a droplet size of approximately 20 nm. When this microemulsion was added into the polymerization mixture the solution lost some of its transparency but did not turn opaque. This indicated that the addition of OTMS to form the silica shell around the particles helps to prevent the interaction of surfactant molecules with the monomer, however it does not prevent the interaction completely and there is still some transparency loss. Hydrogels prepared with Type 2 microemulsions are not completely opaque (higher transmittance values of 19%) demonstrating some improvement in the transparency.

Since the transparency obtained with Type 2 microemulsions was not sufficiently close to the transparency values of a pure p-HEMA hydrogel it was decided to employ other microemulsion systems which would improve the transparency. As explained before, it is suspected that the transparency loss of the polymerization mixture with the addition of microemulsion is due to the interaction of the specific surfactant molecules with HEMA monomer and break-up of the micelle structures. The identification of a surfactant that does not interact with monomer should solve the transparency problem. For that purpose, it was decided to entrap the drug in a Type 3 microemulsion that employs Brij 97 as surfactant. Brij 97 is not as readily soluble as Tween 80 in HEMA. This microemulsion contains about 1% of oil, which is comparably lower than Type 1 and Type 2. However, one can still entrap drugs in comparable concentrations with therapeutic levels. Light scattering studies (FIG. 4) showed that the microemulsions have a droplet size of approximately 9 nm that is suitable for contact lens applications. Additionally, resulting microemulsion does not have a color as in Types 1 and 2. When the microemulsion is added into the polymerization mixture containing monomer, initiator and cross-linker, the solution lost its transparency slightly, however not as drastically as in Type 1. This shows that Brij 97 also has some level of interaction with HEMA. The transparency of the hydrogels synthesized with Type 3 microemulsion was measured as 66% which is higher than the transparency of the hydrogels synthesized with Type 1 and Type 2 microemulsions.

Since one could prevent the interaction of surfactant molecules to some extent in the case of Type 2 microemulsion, it was decided to introduce OTMS to Type 3 microemulsions to form a silica shell around the oil droplets to stabilize them. This microemulsion was designated as Type 4. The silica shell formed around the hexadecane molecules prevents the interaction of Brij 97 molecules with HEMA. The resulting microemulsion was a completely transparent, colorless solution with a mean droplet size of about 15 nm (FIG. 5) that is again small enough to use successfully in contact lens applications. When this microemulsion was added into the polymerization mixture, no transparency loss was observed. Hydrogels synthesized with this microemulsion have about 79% transparency. This is the highest transparency value obtained for the four hydrogels synthesized with four different microemulsions. This transmittance value is very similar to the 87% transmittance value of pure p-HEMA hydrogels. The transparency of liposome laden gels is about the same as that of Type 4 laden gels. The difference in the transmittance for a pure HEMA and Type 4 or liposome loaded HEMA hydrogels will become smaller for contact lenses which are about 10 times thinner than the lenses that were employed in transmittance measurements. As it is clearly seen from FIG. 6, hydrogels synthesized with Type 4 microemulsion or with liposomes are the most promising hydrogels for contact lens applications with respect to transparency.

Drug Release Studies

After synthesizing drug-loaded hydrogels, the rates of drug release from the hydrogel matrix were measured. Initial drug diffusion measurements were performed with the drug, Lidocaine. Lidocaine hydrochloride is an anti-arrhythmic drug commonly used to restore a regular heartbeat in patients with arrhythmia. Lidocaine hydrochloride ($C_{14}H_{22}N_2O \cdot HCl$) is a water-soluble drug that can be converted to an oil soluble form by reacting it with a base such as sodium hydroxide. It can thus be used as both a hydrophilic and a hydrophobic drug. It is contemplated that any of the ophthalmic drugs including Timolol, a non-selective beta-adrenergic receptor blocking agent which treats glaucoma, Cyclosporin A, a lipophilic cyclic polypeptide that has shown promising results in the treatment of dry eye symptoms and Ciproflaxin, which is a synthetic broad spectrum anti-microbial agent, steroids such as Prednisilone acetate which are used for treating macular edema, Acular and Voltaren which are non-steroids that also treat macular edema, antibiotics such as Ciloxan, Gentamycin, Cephlosporins, other glaucoma treatments such as Trusopt, Alphagen and several other ophthalmic drugs would also be operable As explained before, the drug release data is obtained by synthesizing two different hydrogels: one has drug molecules entrapped inside nanoparticles and the other one termed "blank" that also contains the nanoparticles but does not have drug dissolved inside the nanoparticles. The only difference between a drug loaded hydrogel and a blank is the presence of drug molecules in the former. Therefore when UV-Visible measurements are carried out with both hydrogels inserted into the water and the absorbance values obtained for the blank are subtracted from that of the drug loaded hydrogel, the only contribution to the absorbance is that from the drug released into the water.

FIG. 7 shows the long term Lidocaine release data obtained from a hydrogel synthesized by directly dissolving the drug molecules inside the polymerization solution with a hydrogel that was prepared by dissolving Lidocaine molecules in the oil phase of Type 4 microemulsion. Both the gels release almost 100% of the entrapped drug in about 6-7 days. The amount of drug release in the case of direct dissolution is much higher compared to the hydrogel synthesized with Type 4 microemulsion nanoparticles (The microemulsion used in these experiments had about 3% oil). This is because of the exceptionally high solubility of oil soluble form of Lidocaine in the monomer and it is not typical of all hydrophobic drugs that we are planning to entrap in the contact lens matrix. In addition to that, it is not known the extent to which the Lidocaine released from the hydrogel was destroyed during polymerization and the concomitant extent to which it still preserves its functionality. Furthermore the gels used for the experiments reported in FIG. 7 are about 1-mm thick, while contact lenses are about 100-microns thick. The only resistance to drug transport for the case of direct dissolution is diffusion through the gel, which scales inversely as the square of the thickness. As shown in FIG. 7, a 1-mm thick gel loaded with drug by dissolution releases drug for about 8 days, and thus a 100 micron thick contact lens will only release drug for about 0.08 days. In the case of particle laden lenses, since particles control the long time release rates, the time of release is relatively independent of the lens thickness. As seen in FIG. 8, the short time release rates for the case of direct dissolution scale as $t^{1/2}$ which shows that the release rates are controlled by drug diffusion through the gel.

FIG. 9 shows the amount of drug released from hydrogels loaded with particles of Type 2 and Type 4 microemulsions for a time period of 10 days. The Type 3 and 4 microemulsions used in these experiments had about 1% oil (before HCl addition). The drug release experiments were performed only for Type 2 and Type 4 hydrogels since it has already been shown that addition of OTMS layer enhances the transparency by stabilizing the nanoparticles and therefore the particles that have an OTMS layer around them are suitable candidates for drug delivery. For the drug delivery experiments described in FIG. 9, the same concentration of drug is introduced into each hydrogel. Reproducibility experiments yield results with an error of ±7-8%. As it is seen from the figure, the amount of drug released from the Type 2 hydrogel is about the same as that released by the Type 4. Type 2 microemulsions have a much lower transparency value than Type 4 microemulsions. This implies that the morphology and the pore size of the hydrogels obtained with different microemulsions are different from each other and this leads to differences in diffusion. However this difference in microstructure does not lead to significant different in drug release profiles for 1-mm thick gels. As shown in the FIG. 9, drug concentration in water increase rapidly at the beginning of the experiment and level off as the time increases for both the hydrogels. At the end of the experiment both types of gels release about 100% of the entrapped drug. The drug concentration in water varies almost as $t^{1/2}$ implying that the diffusion resistance in the hydrogel is controlling the drug release at short times. However at longer times the drug release rates are controlled by the particles. Release rates are very high during the first day, and after the first day they became considerably slower than the short-term release rates. After a 10 day period, concentration of drug in water levels off, implying an equilibrium between the drug concentration in oil drops, the concentration in the hydrophilic hydrogel matrix and the concentration in water. This behavior of the data implies the presence of two different time scales that can be fitted into two exponential curves with an equation of the form:

$$C_1(1-e^{-t/\Gamma_1})+C_2(1-e^{-t/\Gamma_2})$$

where $C_1$ and $C_2$, $\Gamma_1$ and $\Gamma_2$ are empirical constants.

FIG. 10 shows the drug release data obtained for Type 3 hydrogels synthesized with different drug concentrations. The microemulsion used in these experiments had about 1% oil and the drug loading in the three gels is: 0.42, 0.3 and 0.17 g of drug for each gram of gel. At the end of the 9 day period, almost 100% of the drug initially introduced released into water for each hydrogel. Additionally, drug release profiles are very similar for each drug concentration. This shows that concentration of the drug inside the hydrogel does not affect the fraction of the drug released. This is an expected result. We do not expect that the amount of drug introduced into the hydrogel matrix would cause any significant changes in morphology or particle property changes since it is introduced inside the particles and would not be expected to interact with the hydrogel matrix.

FIG. 10 shows the drug release profiles obtained by dispersing DMPC liposomes in the gel instead of the microemulsion drops. The gels used in this experiment were loaded with 1.3 mg of drug for each gram of gel. Thus we can trap a much larger amount of drug in liposomes than in Type 4 laden gels. This data also shows that depending on the required dosage we can chose nanoparticles different types of nanoparticles. The gels loaded with liposomes have about 79% transmittance which is about the same as Type 4 gels.

The usual starting dose of Timolol which is a hydrophobic ophthalmic drug is one drop of 0.25% timolol maleate in the affected eye(s) twice a day. Assuming a volume of 25 µl for each drop, the daily dosage of Timolol is 0.125 mg each day. Only about 5% of this amount actually reaches the cornea. Thus, the dosage that needs to be delivered to cornea is about 0.0063 mg each day. At a loading of 1.1 mg 1.3 mg of drug per gram of gel which are the loadings in our gels for the 3% microemulsion and the liposomes, respectively, a contact lens can contain about 0.022-0.026 mg of drug. Thus, the lens can supply therapeutic levels of drug delivery for about 4 days. We do note a fraction of the drug incorporated in the contact lens may still be lost to tear drainage. We can further increase this loading by increasing the particle fraction in the gel.

SEM studies were undertaken in order to gain an understanding of the structure of the hydrogels and to see the particles entrapped inside of the hydrogel matrix. As explained before, the sample preparation methods performed for SEM imaging have the potential of introducing artifacts. The samples were dried under vacuum to eliminate any remaining water in the structure. This may cause the shrinkage of the pores once occupied by the water or oil molecules leading to a change in the morphology of the hydrogels. In order to determine whether this is the case, optical microscope images of the hydrogels were taken before and after treatment with liquid nitrogen and vacuum drying. Optical microscope images showed that the structure does not change with the sample treatment. Therefore, the SEM images discussed below show the structure after polymerization in dry state.

FIG. 12 shows the SEM picture of a pure p-HEMA hydrogel. The surface of a pure p-HEMA hydrogel is rather smooth and non-porous and no grain boundaries are observed. However, the picture of a hydrogel loaded with particles of Type 1 microemulsion (FIG. 13) shows a rather rough surface with enhanced grain boundaries. This drastic change in the structure of the hydrogel with the addition of Type 1 microemulsion can be attributed to the fact that surfactants of this microemulsion are soluble in the monomer. As a result of this, most of the particles are destroyed when they are introduced into the polymerization mixture leaving the oil phase free. Oil phase accumulates at the grain boundaries during cross-linking and cause a phase separation leading to the enhanced grain boundary structure observed in the SEM image. Only nanoparticles that are not dissolved in the monomer get entrapped in the cross-linked structure. This highly enhanced grain boundary structure leading to the phase separation explains the low transparency values observed for this hydrogel.

The SEM image of the Type 2 hydrogel (FIG. 14) shows a different structure than both pure p-HEMA and Type 1 hydrogel. Thus, the image shows big holes (~4000 nm size) on the surface with the smooth surrounding area instead of the highly enhanced grain structure observed in the case of Type 1 hydrogel. This difference in the surface morphology of these two hydrogels must be because in this case we are introducing a silica shell around the particles to stabilize and prevent the interaction of surfactant molecules with the HEMA monomer. The silica shell prevents the solubilization of the surfactants in the monomer to some extent. However it is not strong enough and some particles agglomerate together forming big clusters of nanoparticles. During vacuum drying after synthesis, some of these big clusters of oil molecules evaporate forming the big holes observed at the surface. This particle agglomeration must be the reason for the low transparency values observed for this kind of hydrogel. When particles agglomerate, they become large in size and they start to scatter the visible light causing the loss of transparency.

FIG. 15 shows the surface image of a Type 3 hydrogel. It looks similar to the surface image of a pure p-HEMA hydrogel with the exception that grain boundaries are observable in this case although they are not enhanced as in the case of Type 1 and Type 2. This implies that since surfactants of this microemulsion do not dissolve in the monomer they do not break and segregate at the phase boundaries causing a phase separation. This explains the much higher transmittance values of this type of hydrogels. Also, since the particles are more stable, there will be less particles that are broken and will be released in short time scale, leading to lower release rates in the short time scale compared to Type 1 and Type 2 hydrogels.

In case of Type 4 microemulsions (FIG. 16), the structure is almost like a pure p-HEMA hydrogel as expected because of the very high transparency value obtained for this hydrogel. In this microemulsion, the introduction of the silica shell prevents the interaction of particles with each other sufficiently enough that particles do not agglomerate to form big clusters causing the loss of transparency. In addition to that, the amount of particles that is destroyed due to the solubilization of surfactant molecules in the monomer is lower than is the case with any other drug loaded hydrogel so that one achieves a much lower short time release rate for this hydrogel than a Type 2 hydrogel (FIG. 15).

SEM pictures at higher magnifications enable one to see the particles inside of the drug-loaded hydrogels. We would also be able to see the spots left by the particles evaporated and leave the surface during vacuum drying (FIG. 14) and spherical nanoparticles (FIGS. 17-19). These pictures showed success in entrapping the microemulsion particles in the hydrogel matrix. Size of these drop-like structures is about 300-400 nm in FIGS. 17 and 18, i.e., 15-20 times more than the size of a single microemulsion droplet. This implies that these particles seen on the figures must be clusters of several particles aggregated together. This kind of cluster formation is expected for Type 1 and Type 2 hydrogels along with the complete breakup of the particles. These are particles strong enough not to completely break down but still aggregated to some extent. We could not observe smaller, microemulsion droplet size particles in these two hydrogels. FIG. 19 shows nanoparticles dispersed in a Type 4 hydrogel matrix. The particles have sizes around 30-50 nm that is close to the size of a single microemulsion droplet.

Looking at FIGS. 17-19, it can be seen that the particles occur in two different regions in the hydrogel matrix. Some particles in FIGS. 17 and 18 are observed at the grain boundaries and it is easy for drug to diffuse out of these particles to the eye since they do not have the resistance of the cross-linked p-HEMA structure against drug diffusion. These particles observed basically in Type 1 microemulsion. Other particles are entrapped inside the cross-linked hydrogel matrix, and these contribute to the long-term release. The reason for the occurrence of the particles in these two regions could be explained as follows. During the polymerization process, cross-linked polymer grain grows and at some point it meets with a nanoparticle. Nanoparticles are free to move in the polymerization mixture having the freedom to move in every direction. There are two possibilities: First, the particle and the growing chain may have an attraction to each other. In this case, since the particle is free to move in every direction, it would prefer to diffuse towards to growing chain and it ends up getting entrapped inside the cross-linked structure. Particles entrapped that way are evenly distributed in the hydrogel matrix and they do not cause the loss of transparency since they stay as single particles and do not segregate. This type of formation may also occur if there is no attraction between the particle and the growing chain but the reaction is much faster than diffusion so that chain grows onto particle before it has any chance to diffuse out. These kinds of particles are more likely in the case of Type 2 and Type 4 hydrogels since silica shell around the particles prevents the interaction between monomer and surfactant molecules.

Another explanation is that, if there is no attraction between the growing chain and the nanoparticles and reaction is slower than diffusion, since the particles are free to diffuse in every direction, they may prefer to diffuse out of the growing chain. Other chains will be growing at the same time and these particles will be forced to remain in the grain boundaries. The nanoparticles that are not destroyed would prefer to stay at the grain boundaries forming big clusters of particles. These clusters are also observed for Type 2 hydrogels since silica shell is not efficient enough to prevent the interaction. We did not observe formation of Type 1 particle entrapment in the case of Type 3 and Type 4 hydrogels.

Drug release studies and SEM pictures showed success in entrapping the lipophilic drug, Lidocaine, in p-HEMA hydrogel matrices. Long-term release rates were obtained, comparable to the therapeutic levels with Type 4 and liposome hydrogels. These hydrogels released drugs for about 8 days. The release rates and total amount of drug that can be introduced into the eye were even higher in the case of Type 2 hydrogels. Type 4 microemulsion and liposomes gave the most promising results in terms of transparency. Although the final amount of drug released at the end of a 10 day period was much lower for Type 4 microemulsion than Type 1 and Type 2, the amount and rates were still enough to supply drug for at least a few days to the eye. The amount entrapped can be further increased by increasing the fraction of particles.

The formation of a silica shell around the microemulsion droplet acts to prevent the interaction between surfactant molecules and monomer that cause the loss of transparency. This interaction and an increase in transparencies can be achieved by either increasing the thickness of the shell or by adding other chemicals to form stronger shells.

Thus, in accordance with the principles of the present invention, drugs can be entrapped in hydrogel matrices that can be used to deliver ophthalmic drugs via contact lenses. The drug delivery rates can be controlled by tailoring the microstructure of the hydrogel and manipulating the size, concentration and structure of the nanoparticles and the concentration of the drug in the particles.

The invention claimed is:

1. A drug delivery system comprising a contact lens having dispersed throughout as nanoparticles an ophthalmic drug nanoencapsulated with an encapsulation material, wherein said encapsulation material is selected dependent upon ophthalmic drug characteristics wherein a hydrophobic encapsulation material is selected for a hydrophobic ophthalmic drug and a hydrophilic encapsulation material is selected for a hydrophilic ophthalmic drug; wherein said ophthalmic drug is capable of diffusion into and migration through said contact lens and into the post-lens tear film when said contact lens is placed on the eye; wherein said diffusion results in extended or time-release delivery of said ophthalmic drug; and wherein said nanoparticles are dispersed within said contact lens in an amount such that said contact lens remains optically transparent, wherein optically transparent is a degree of transparency equal to that of p-HEMA or other material employed as a contact lens.

2. The drug delivery system of claim 1, each said nanoparticles having a particle size less than about 50 nm.

3. The drug delivery system of claim 2 wherein said amount of nanoparticles is from about 1 to about 5%, by weight, based on the weight of the contact lens.

4. The drug delivery system of claim 1 wherein said contact lens comprises poly 2-hydroxyethylmethacrylate, and wherein the transmittance of visible light through said contact lens is at least 66%.

5. The drug delivery system of claim 1, wherein said hydrophilic encapsulation material is a liposome.

6. The drug delivery system of claim 1 wherein said ophthalmic drug is an antiparisitic, a steroid, a non-steroidal anti-inflammatory, an antibiotic or mixtures thereof.

7. The drug delivery system of claim 1 wherein said ophthalmic drug is nanoencapsulated with an encapsulation material in an oil-in-water emulsion hydrophobic encapsulation material is a microemulsion.

8. The drug delivery system of claim 7, wherein said encapsulation material comprises: chitosan, human serum albumin, biodegradable poly(alkylcynoacrylates), polybutylcyanoacrylate, polyhexylcyanoacrylate, polyethylcyanoacrylate, (polyisobutylcyanoacrylate), polycyanoacylate, silica, PEG'ylated core-shell, biodegradable PLGA (poly(D,L-lactide-co-glycolide)), (poly lactic acid), PGA, PLG (poly(D,L-glycolide))polymeric, microemulsion, liposomes, biocompatible gliadin, low pH sensitive PEG stabilized plasmid-lipid, biodegradable calcium phosphate, legumin, tocopherol derivatives stabilized emulsion, polysaccherides grafted with Polyesthers (amphyphilic copolymers), PLA-PEG, hydrophilic proteins coupled with apolipoprotein E, biodegradable poly(vepsiln-caprolactone), poly(methylidene malonate), gelatin, poly(E-caprolactone), sodium alginate, agarose hydrogel, PMMA, biotinylated poly(ethylene glycol) conjugated with lactobionic acid, carboxylmethyl dextran magnetic, poly(vinyl alcohol)hydrogel, biotinylated pullulan acetate, diblock copolymers or mixtures thereof.

9. A method of administering an ophthalmic drug to a patient in need thereof comprising placing on the eye thereof the drug delivery system of claim 1.

10. A kit comprising:
   a) a first component containing the drug delivery system of claim 1, and
   b) a second component containing at least one storage container for said first component, said storage container additionally containing a material that substantially prevents said diffusion and migration of said ophthalmic drug during storage.

11. The kit of claim 10 wherein said material that substantially prevents said diffusion and migration of said ophthalmic drug is substantially saturated with an aqueous solution of said ophthalmic drug.

12. The kit of claim 11, wherein the kit is used for the storage and delivery of ophthalmic drugs to the eye of a patient in need thereof.

13. A method of preparing the drug delivery system of claim 1 comprising:
   a) providing said nanoencapsulated ophthalmic drug, and
   b) preparing said contact lens from materials that incorporate the nanoencapsulated ophthalmic drug, such that the nanoencapsulated ophthalmic drug is substantially uniformly dispersed throughout said contact lens.

14. An article of manufacture comprising packaging material and the ophthalmic drug delivery system of claim 1 contained within said packaging material, wherein said packaging material comprises a label which indicates that said ophthalmic drug delivery system can be used for ameliorating symptoms associated with pathologic conditions of the eye.

15. An article of manufacture comprising packaging material and the kit of claim 12 contained within said packaging material, wherein said packaging material comprises a label which indicates that said first component of said kit can be used for ameliorating symptoms associated with pathologic conditions of the eye and that said second component of said kit can be used for storage of said first component.

16. The drug delivery system of claim 6 wherein said antiparisitic drug is ivermectin, pyrimethamine or mixtures thereof.

17. The drug delivery system of claim 6 wherein said steroid is prednisilone acetate.

18. The drug delivery system of claim 6 wherein said non-steroidal anti inflammatory drug is acular, voltaren, or mixtures thereof.

19. The drug delivery system of claim 6 wherein said antibiotic drug is ciloxan, gentamycin, cephlosporin or mixtures thereof.

20. The drug delivery system of claim 1 wherein said ophthalmic drug is lidocaine, timolol, ciproflaxin, cyclosporin A, or pilocarpine.

21. The drug delivery system of claim 2 wherein said nanoparticles are dispersed within said contact lens from about 5 to about 20%, by weight, based on the weight of the contact lens.

* * * * *